(12) United States Patent
Schiffman

(10) Patent No.: US 6,346,085 B1
(45) Date of Patent: Feb. 12, 2002

(54) SOFT TISSUE BIOPSY INSTRUMENT

(76) Inventor: Noah I. Schiffman, 158 Wentworth St., Apartment 3, Charleston, SC (US) 29401

( * ) Notice: Subject to any disclaimer, the term of this patent is extended or adjusted under 35 U.S.C. 154(b) by 0 days.

(21) Appl. No.: 09/604,360

(22) Filed: Jun. 27, 2000

(51) Int. Cl.[7] ............................................. A61B 10/00
(52) U.S. Cl. ....................... 600/565; 600/564; 600/170
(58) Field of Search .................................. 600/564, 565, 600/566, 567, 571; 606/119, 167, 170, 114, 115; 83/915.5; D24/146, 147

(56) References Cited

U.S. PATENT DOCUMENTS

| | | | | |
|---|---|---|---|---|
| 4,656,999 A | * | 4/1987 | Storz ........................... | 600/104 |
| 5,090,419 A | | 2/1992 | Palestrant .................... | 600/567 |
| 5,161,542 A | | 11/1992 | Palestrant .................... | 600/567 |
| 5,213,110 A | * | 5/1993 | Kedem et al. ............... | 600/567 |
| 5,273,026 A | | 12/1993 | Wilk ............................ | 600/206 |
| 5,357,980 A | | 10/1994 | Seitzinger ................... | 128/837 |
| 5,373,854 A | | 12/1994 | Kolozsi ....................... | 606/562 |
| 5,409,496 A | | 4/1995 | Rowden et al. ............. | 606/119 |
| 5,483,952 A | * | 1/1996 | Aranyi ......................... | 600/131 |
| 5,520,698 A | | 5/1996 | Koh ............................. | 606/119 |
| 5,643,285 A | | 7/1997 | Rowden et al. ............. | 606/119 |
| 5,643,307 A | | 7/1997 | Turkel et al. ................ | 606/184 |
| 5,810,806 A | * | 9/1998 | Ritchart et al. ............... | 606/45 |
| 5,827,305 A | * | 10/1998 | Gordon ....................... | 606/159 |
| 5,840,077 A | | 11/1998 | Rowden et al. ............. | 606/119 |
| 6,053,877 A | * | 4/2000 | Banik et al. ................. | 600/566 |
| 6,068,603 A | * | 5/2000 | Suzuki ........................ | 600/565 |
| 6,280,398 B1 | * | 8/2001 | Ritchart et al. ............. | 600/564 |

OTHER PUBLICATIONS

Coopersurgical,"CooperSurgical Office and Colposcopy Products", Catalog, 1999, CooperSurgical, Inc., Euro–Med Biopsy Punch Series, USA.

* cited by examiner

Primary Examiner—John P. Lacyk
Assistant Examiner—Charles Marmor, II
(74) Attorney, Agent, or Firm—Harleston Law Firm; Kathleen M. Harleston

(57) ABSTRACT

A surgical instrument for biopsying soft body tissue includes: (1) a distal barrel section, which includes: (a) a hollow barrel having an open, distal end and a proximal end; (b) a piston rod which movably extends substantially through the barrel; (c) a cutting mechanism coupled to the distal end of the barrel, which includes a movable surgical blade; (d) a trigger mechanism coupled to the cutting mechanism for releasing the movable blade; and (2) a proximal handle section coupled to the barrel and the piston rod. When the proximal handle section is compressed by a user, the piston rod retracts, and suction is created within the distal end of the barrel. When the trigger mechanism is pulled by the user, the movable blade moves from an open, ready position to a closed position, and the tissue sample is excised.

16 Claims, 10 Drawing Sheets

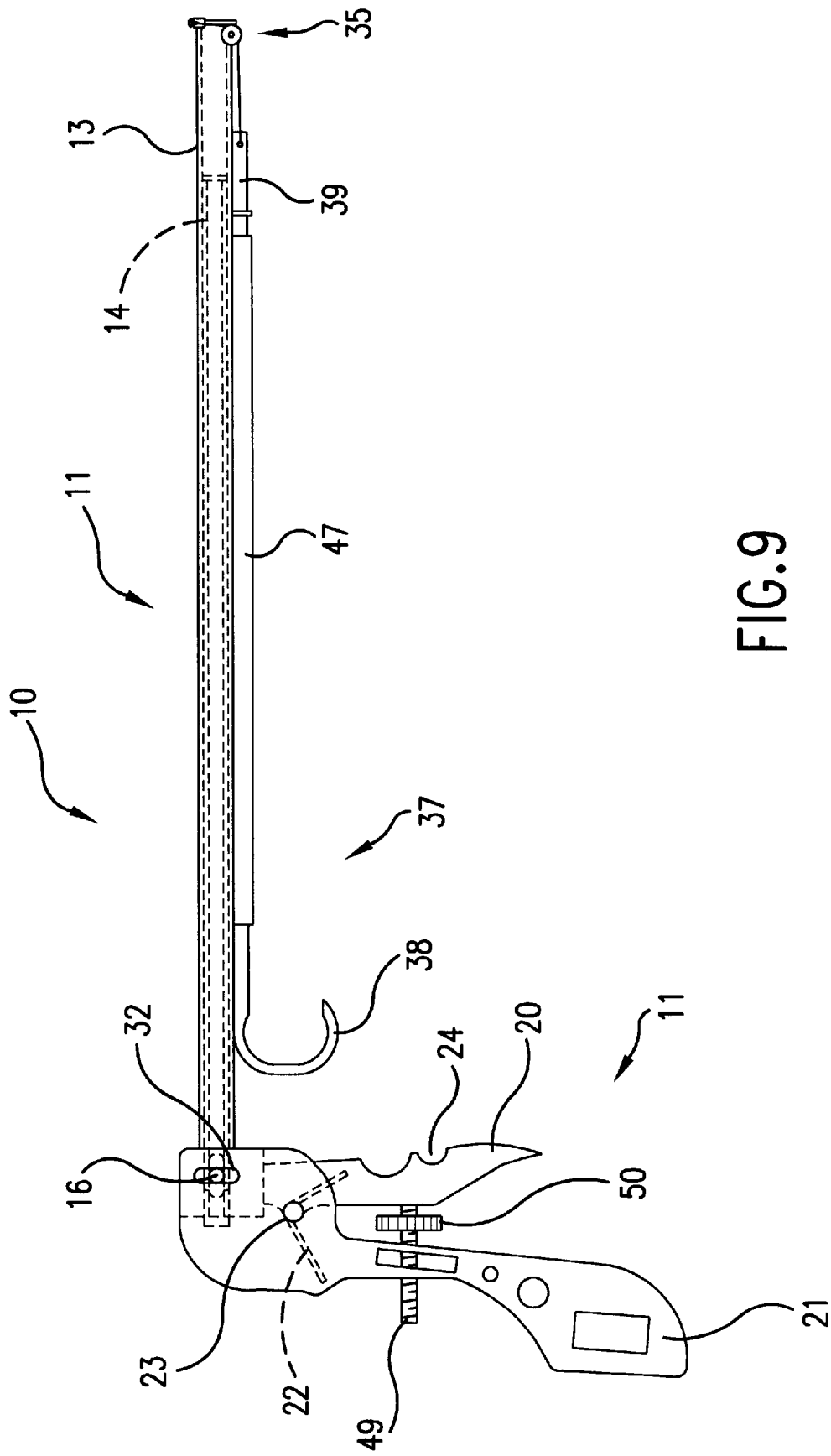

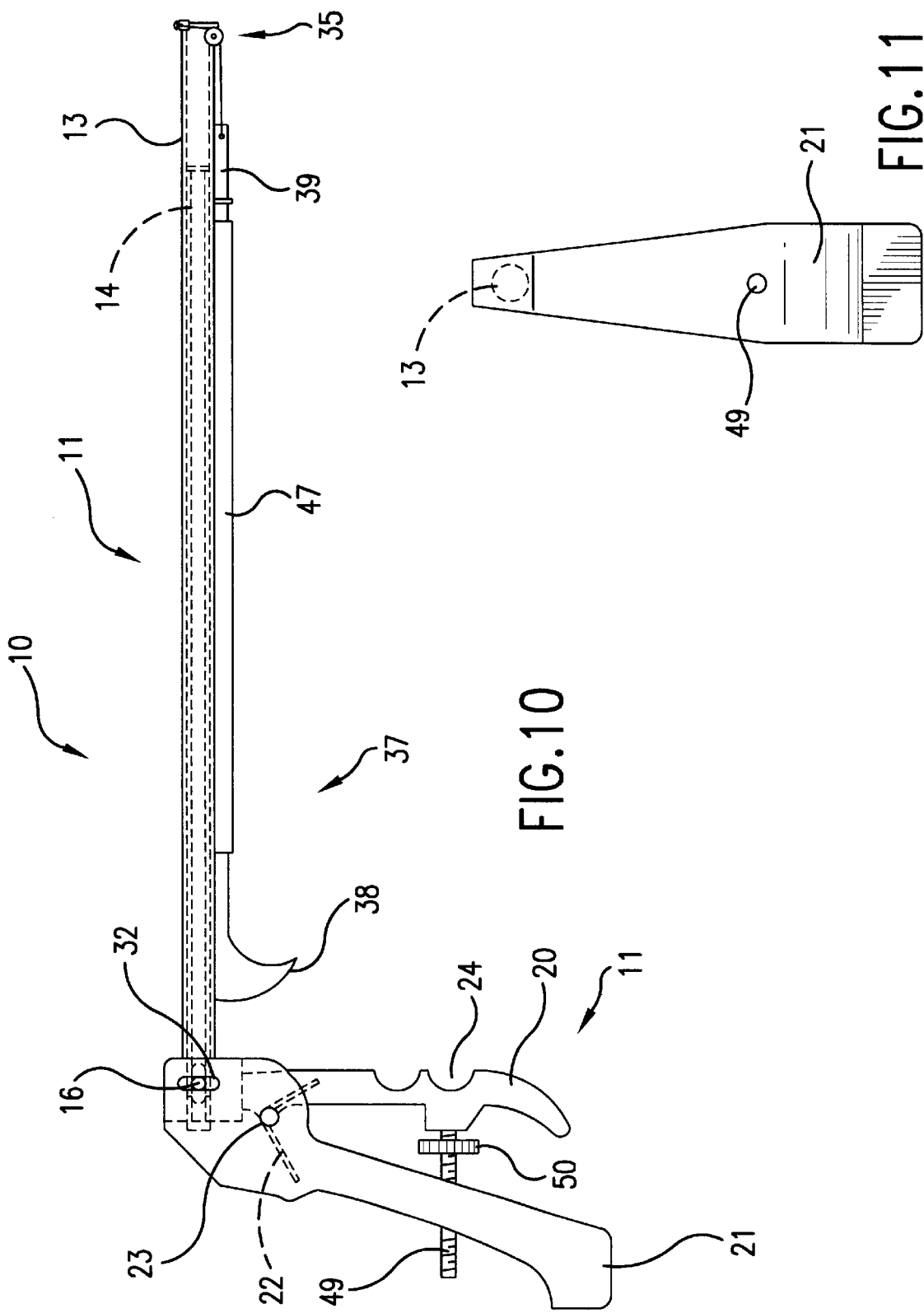

SOFT TISSUE BIOPSY INSTRUMENT

BACKGROUND OF THE INVENTION

1. Technical Field

The present invention relates in general to surgical instruments, and more particularly to biopsy instruments for excising and collecting single or multiple cervical or other soft tissue samples.

2. Background Information

A common out-patient surgical procedure conducted by gynecologists and other physicians is the cervical biopsy. Generally, the procedure involves inserting a speculum through the vagina, and then inserting the distal end of a colposcope into the vaginal opening. A colposcope magnifies the view and shines a light onto the surface of the cervix. The physician methodically views each quadrant of the cervix through the colposcope. Usually, a sterile swab is used to brush a thin coating of dilute acetic acid (vinegar), iodine (Lugol's solution), or other staining solution over the cervical surface. The physician then immediately views the same area, looking for any whitish, dotted patches along the surface of the cervix, which indicate dysplasia. These findings are charted. A small camera may be attached to the colposcope, if photos are desired. Acetowhite patches usually indicate abnormal cells, which may be cancerous. If abnormal-looking areas are observed during colposcopy, the physician is likely to recommend biopsy of the area. The physician may also observe lesions or other irregularities in the cervical area, which may indicate disease pathology. The size and shape of any lesions, their response to staining, and their color and degree of vascularization are recorded.

Biopsy samples are ordinarily examined under a microscope. The pathologist or technician in the hospital or clinical laboratory first uses a microtome or similar instrument to shave off a thin layer of cells from the tissue sample. The tissue layer is fixed on a slide, and then placed under the microscope. Each sample is carefully examined for any abnormal cells that may indicate a cancerous or precancerous condition. The patient's physician will be given a pathology report containing the results for each tissue sample. The physician analyzes these results, along with the colposcope observations and Pap smear results, to diagnose whether cervical dysplasia, or another disease, may be present. These results may warrant further steps, such as a cone biopsy, cryotherapy, laser ablation, or possibly radiation therapy or surgical intervention.

Only a very thin layer of tissue (several cell layers thick) is necessary for evaluation by the pathologist. Pulling off large samples from the cervix is unnecessary and may be associated with adverse side effects. This appears to be one of the problems with existing instruments for biopsying cervical tissue: they tear off tissue samples that are often irregular in shape and larger than necessary. Many conventional colpotomy instruments possess small cutting jaws at the distal end which are pushed into the relatively flat cervical surface in order to grasp a section of tissue. The physician then uses the handle to close the jaws. The jaws clench the section of tissue and tear it from the cervix. The colpotomy instrument is withdrawn from the cervix and the sample is transferred from the jaws of the instrument to a sample container. The instrument is inserted once again to obtain an additional sample from a different area of the cervix, and so forth. The biopsy specimen are all placed in plastic containers, which are then transported to a lab and carefully analyzed.

The conventional instruments, which pull and/or bite the cervical tissue, can damage tissue adjacent to the sample sites and cause excessive cervical penetration, pain, and bleeding. These adverse side effects may be associated with a higher likelihood of infection and other complications. The patient may experience more pain and/or cramping during and after the procedure, particularly if she has preexisting gynecological problems. Although bleeding in the area of the biopsy is normally treated with an iron-containing substance (Monsel's solution) or a solution of silver nitrate, a smaller, more precise biopsy may reduce the necessity for this treatment and would likely decrease vaginal bleeding post-surgically.

The colpotomy instrument of the present invention uses slight suction to pull the cervical tissue into the device end, and then surgically excises a small, precise sample of tissue. In contrast with various types of existing instruments with jaws, the distal end of this instrument need not be pushed into the cervical wall in order to seize a tissue sample. The present instrument allows small, precise, uniformly shaped samples of tissue to be excised, with minimal damage to adjacent tissues. Importantly, the patient experiences less pain, bleeding, and associated discharge during and after the procedure when the instrument of the present invention is used. Morbidity and mortality rates from such procedures, though already low, may be reduced. In summary, the cervical biopsy procedure would be more humane, less painful, more surgically precise, and may be associated with better outcomes when the instrument of the present invention is employed. These numerous advantages may be translated to other soft tissue surgical biopsy procedures.

BRIEF SUMMARY OF THE INVENTION

The present invention is an instrument for biopsying cervical tissue or the like, which comprises:

(1) a distal barrel section, which includes: (a) a hollow barrel having an open, distal end and an opposite proximal end; (b) a piston rod which movably extends substantially through the barrel, the piston rod having a distal end and an opposite proximal end; (c) a cutting mechanism coupled to the distal end of the barrel, the cutting mechanism comprising a movable surgical blade for excising a tissue sample, and having an open, ready position and a closed position; (d) a trigger mechanism coupled to the cutting mechanism for moving the movable blade; and (2) a proximal handle section coupled to the proximal ends of both the barrel and the piston rod. The piston rod retracts from the distal end of the barrel when the proximal handle section is compressed by a user. When the trigger mechanism is pulled by a user, the cutting mechanism moves from the open position to the closed position.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein:

FIG. 9 is a side elevational view of a second alternate embodiment of a biopsy instrument according to the present invention;

FIG. 10 is a side elevational view of a third alternate embodiment of a biopsy instrument according to the present invention;

FIG. 11 is a rear elevational view of a biopsy instrument according to FIG. 10.

DETAILED DESCRIPTION OF THE INVENTION

Figure 1:
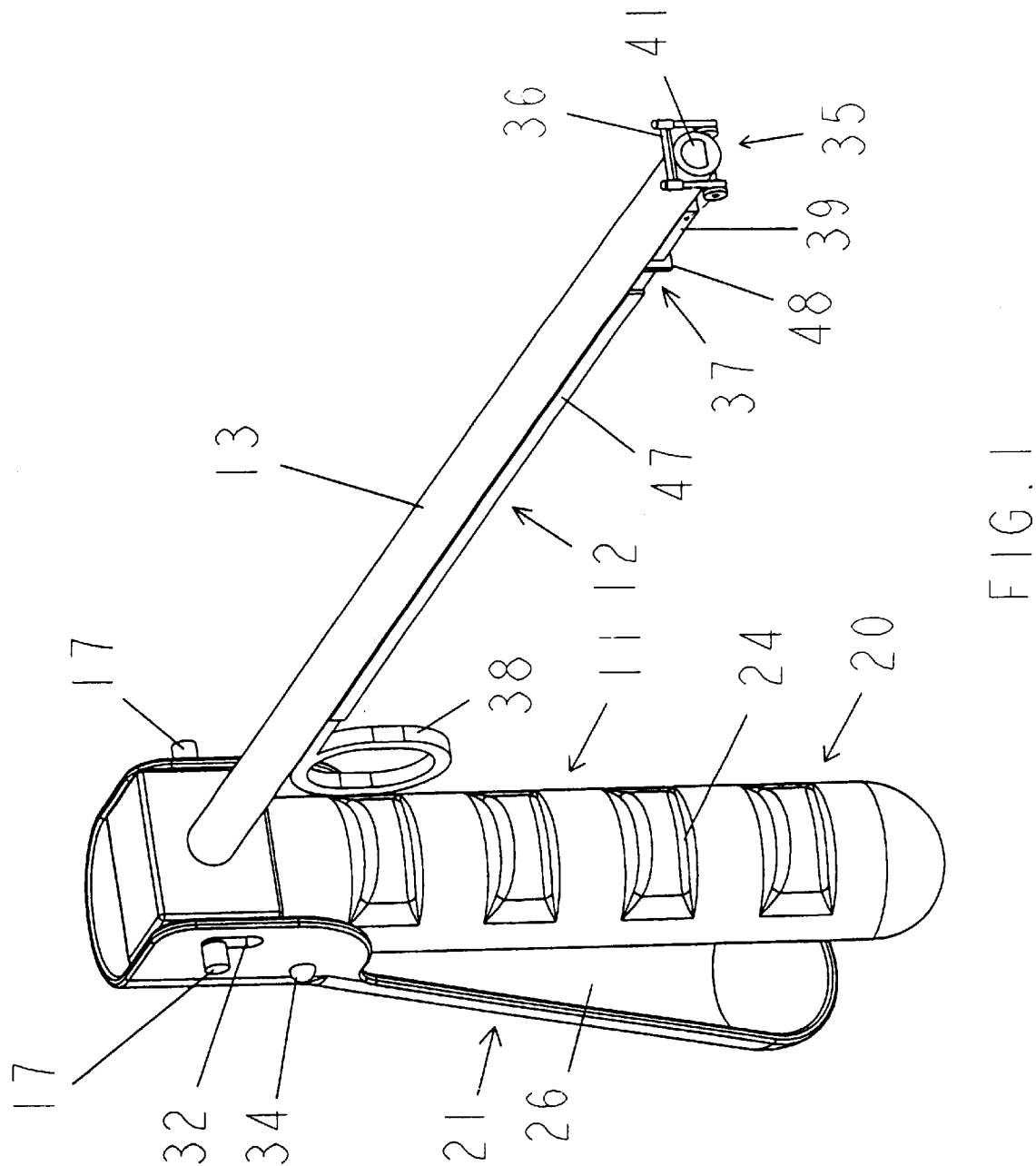
FIG. 1 shows a front perspective view of a biopsy instrument according to the present invention, shown in an open position.

In the following description, like reference characters designate like or corresponding parts throughout the several views. Also, in the following description, it is to be understood that such terms as "front," "back," "within," and the like are words of convenience and are not to be construed as limiting terms. Referring in more detail to the drawings, the invention will now be described.

Figure 2:
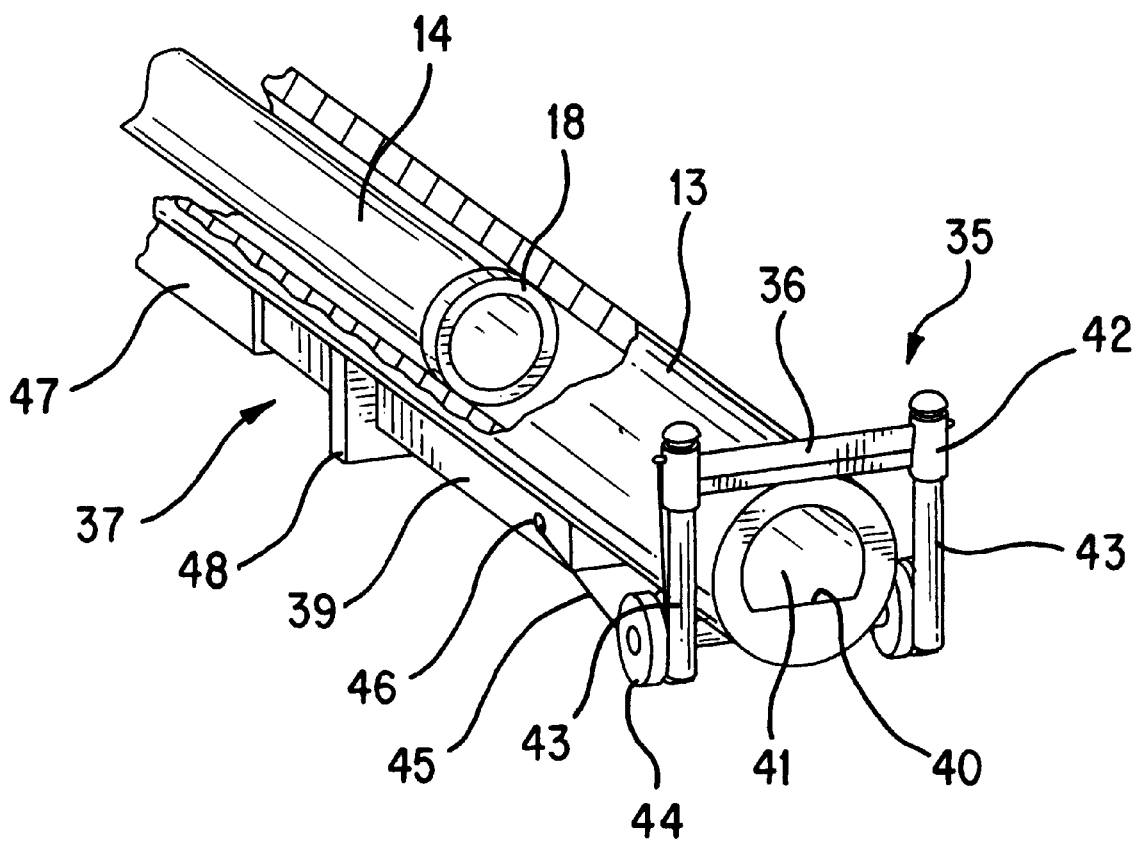
FIG. 2 is a front perspective view of the distal end of a biopsy instrument according to FIG. 1.
Figure 3:
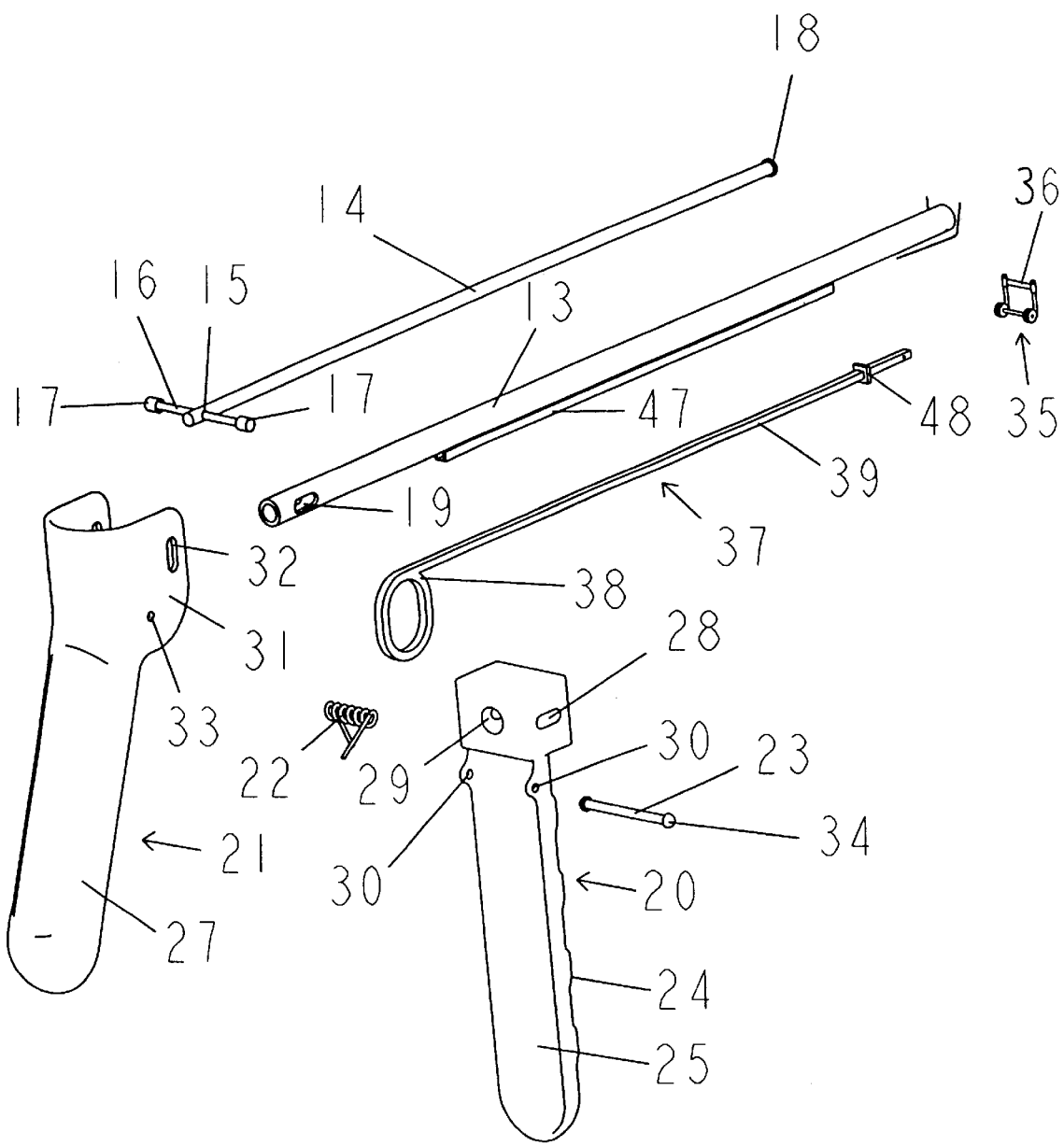
FIG. 3 is a rear perspective view of the disassembled parts of a biopsy instrument according to FIG. 1.

Referring to FIGS. 1 through 3, a surgical instrument 10 according to the present invention for taking biopsies from a cervix, or a similar type of soft body tissue sample, includes two general sections: a proximal handle section 11, which is coupled to a distal barrel section 12. FIG. 1 shows the instrument with the handle section 11 in an open position, FIG. 2 shows the distal end of the barrel section 12, and FIG. 3 shows the disassembled parts of the instrument 10. This colpotomy instrument 10 is made of sturdy, lightweight materials, such as stainless steel, which can be repeatedly autoclaved or otherwise sterilized. This instrument will take several biopsies in succession from a patient.

The instrument 10 includes the proximal handle section 11, which is coupled to proximal ends of both a barrel 13 and a piston rod 14. When the proximal handle section 11 is depressed by a user, the piston rod 14 moves away from the distal end of the barrel, and creates suction within the distal end of the barrel.

As shown in FIG. 2 in dashed lines, the distal barrel section 12 comprises the hollow barrel 13, and the movable piston rod 14, which extends through the barrel 13. The barrel section 12 preferably further comprises: a slide bar 16 at the proximal end of the piston rod 14 which movably extends through a bore in the piston rod, in a direction perpendicular to the piston rod.

As shown in FIG. 3, the proximal end of the piston rod 14 has a bore 15 through which extends the movable slide bar 16. The slide bar 16 is perpendicular to, and much shorter than, the barrel, and fits closely in the piston bore 15. The slide bar 16 can be moved back and forth in the piston bore 15. At each end of the slide bar 16 is a removable slide bar cap 17, shown in FIGS. 1 and 3. The barrel 13 and piston rod 14 are preferably made of stainless steel, and the slide bar caps 17 are preferably made of rubber or a like material. The slide bar caps 17 are either screwed on or snap on the ends of the slide bar 16. The purpose of the slide bar caps is to prevent the slide bar from inadvertently being pulled out of the instrument, which could cause parts of the instrument to become disconnected, and to protect the user and patient from accidental scrapes on the ends of the slide bar, which protrude from either side of the handle. The distal end of the movable piston rod 14 is preferably rubber tipped and flanged. This piston rod flanged tip 18 allows the end of the piston rod to fit closely in the hollow of the barrel, forming an air tight seal.

As shown in FIG. 3, the proximal end of the barrel 13 has an oblong-shaped bore 19 through both sides of the barrel. The oblong bore extends in a horizontal direction along the same plane as the barrel. When the instrument 10 is assembled, the piston rod 14 is in the barrel. The slide bar 16 extends through the oblong barrel bore 19 and the piston rod bore 15, perpendicular to both. The main purpose of the slide bar is to hold the piston rod and barrel in the handle.

When the instrument is in use, the proximal handle section 11 is held by the physician while the distal barrel section 12 extends into the vaginal opening towards the cervix. Generally, the physician interacts with the proximal handle section 11 and the distal barrel section 12 interacts with the patient. The distal end of the barrel section is the point of contact with the cervical wall. The physician views the cervical wall through a colposcope while operating the present instrument with his or her dominant hand.

Figure 4:
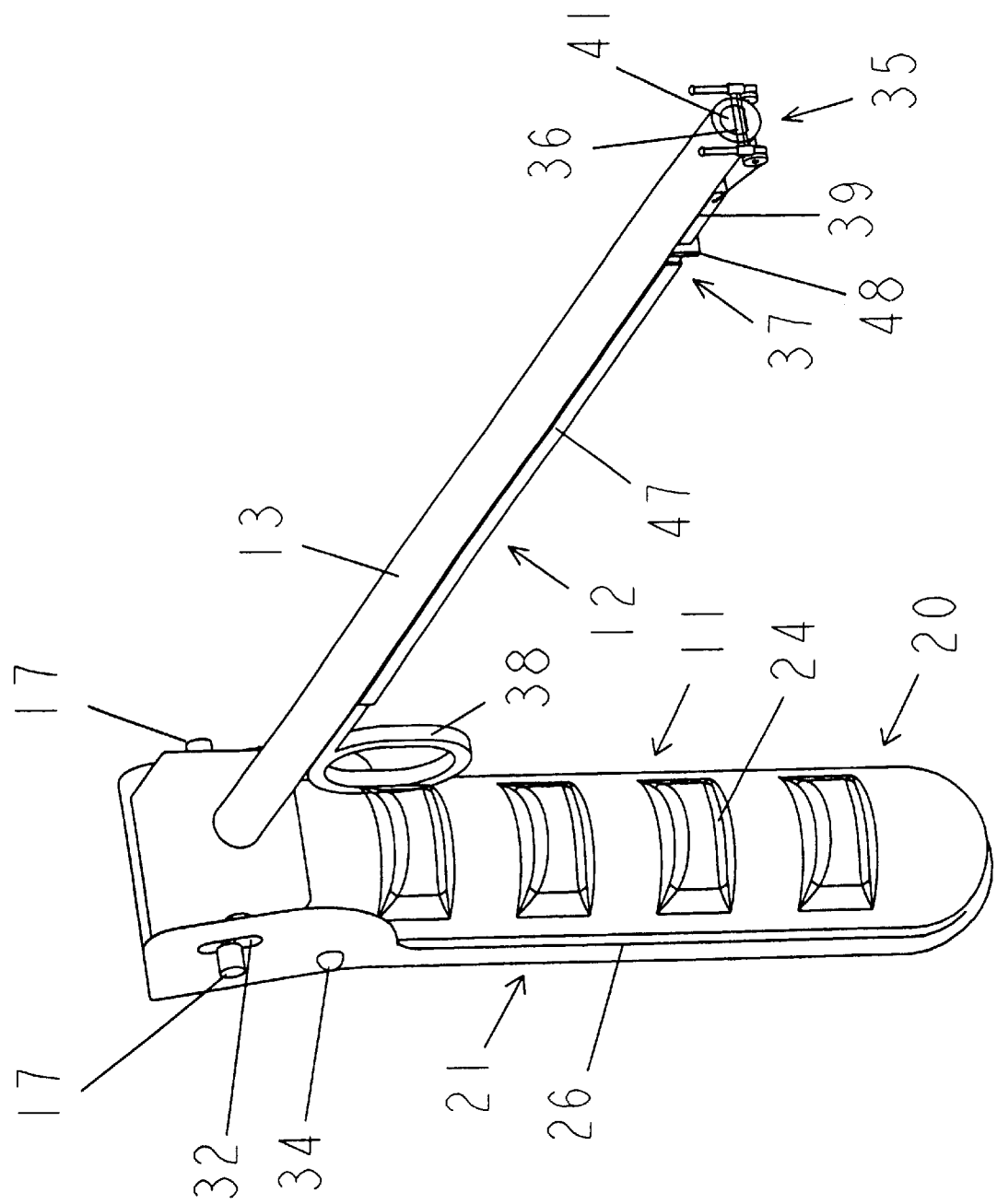
FIG. 4 shows a front perspective view of a biopsy instrument according to the present invention, shown in a closed position.

The instrument is shown in an open, resting position in FIG. 1, and in a closed, engaged position in FIG. 4. In use, the distal end of the instrument 10 is placed against the cervix at the area to be biopsied. The handle is depressed by the physician, which pulls the piston rod 14 away from the distal end of the instrument. As this occurs, the air-tight rubber flange 18 at the distal end of the piston rod creates a vacuum while retracting toward the handle. This vacuum provides suction force, which sucks a small amount of cervical tissue into the distal end of the barrel. Thus, a circle of cervical tissue with the same approximate inside diameter as the barrel protrudes into the end of the barrel 13.

The instrument of the present invention preferably does not have teeth or jaws, and does not punch out a tissue sample.

The proximal handle section preferably comprises: (a) a first handle portion 20 having an upper and a lower end, the upper end being coupled to the proximal ends of the barrel and the piston rod; (b) a second handle portion 21 coupled at an upper end to the upper end of the first handle section; and (c) a spring mechanism 22 pivotally engaged between the first and second handle sections. The piston rod is moved in a proximal direction when the user squeezes the first and second handle portions toward each other.

With continued attention to FIGS. 1 and 3, the proximal handle section 11 comprises four parts: a first handle portion 20, which is coupled to a second handle portion 21, a handle spring mechanism 22, and a handle pin 23. The first handle portion 20 shown in FIGS. 1 and 3 has a block-shaped upper portion end. Its paddle-shaped, lower portion is formed in front with depressions 24 so that it can be easily grasped, even with a gloved hand. These depressions on the first handle portion are shaped to accommodate the last three fingers of the physician's hand. As shown in FIGS. 1 and 3, the first handle portion 20 has a generally flat back (proximal) surface 25, which fits into a concave front (distal) surface 26 on the second handle portion 21. As shown in FIG. 3, the back (proximal) surface 27 of the second handle portion 21 is convex in shape to accommodate the physician's palm when the instrument 10 is in use.

As shown in FIG. 3, the block-shaped upper end of the first handle portion 20 1includes a first, oblong-shaped bore 28, which extends from one side of the handle to the other. A second, central, circular bore 29 extends from the front to the back of the blockshaped upper end. The upper part of the lower end of the first handle portion 20 includes two small matching shoulders, each having a third, small, pin bore 30 therethrough.

Continuing with FIG. 3, the upper end of the second handle portion 21 has two, larger matching shoulders 31 facing forward. Each shoulder has a fourth, oblong-shaped bore 32 through it. These oblong handle bores 32 correspond to the matching oblong barrel bores 19, except that the orientation of the barrel bores lies in the horizontal direction, while the oblong bores of the second handle portion are vertically oriented, that is, perpendicular to the barrel bores. The shoulders 31 also hold two fifth, small, pin bores 33, which correspond to the third, pin bores 30 of the first handle portion 20.

In summary, the first and second handle portions 20, 21 each comprise a matched set of shoulders, with a similarly sized pin bore 30, 33 through each shoulder. The handle spring mechanism 22 is movably affixed between the corresponding shoulders of the first and second handle portions 20, 21. The proximal handle portion 11 preferably further comprises: a movable pin 23 inserted through the matched sets of pin bores 30, 33 in the corresponding shoulders of the first and second handle portions and through the spring mechanism 22.

Further, the upper end of the first handle portion 20 further comprises the second, central bore 29 through which extends the proximal ends of the barrel 13 and the piston rod 14. The first handle 20 portion comprises the first, oblong-shaped bore 28, which is perpendicular to, and intersects with, the second, central bore 29. The second handle portion 21 comprises the matching set of fourth, oblong-shaped bores 32. The slide bar 16 movably extends through the first and fourth, oblong-shaped bores 28, 32 in the first and second handle.portions 20, 21, and through the piston rod bore 15 and the barrel bore 19 in the proximal ends of the piston rod and barrel, respectively.

Lastly, regarding the bores, the oblong shape of the first bore 28 of the first handle portion 20 extends in a horizontal direction, while the oblong shapes of the matching, fourth bores 32 in the second handle portion 21 extend in a vertical direction. When the handle portions 20, 21 are squeezed together, the piston rod 14 moves in a backward rotational movement. The oblong bores 19, 32 allow for the piston rod to move accordingly with respect to both horizontal and vertical movements. The piston rod 14 returns to its forward, resting position when the handle portions 20, 21 are released by the user.

To assemble the instrument after maintenance or sterilization, the technician places the handle spring mechanism 22 between the third, pin bores 30 of the first handle portion. The shoulders 31 of the second handle portion 21 are placed over the first handle portion 20 so that the fifth, pin bores 33 and third, pin bores 30 are aligned. The handle pin 23 is placed through the bores 30 and 33, and the center coil of the spring mechanism 22. Like the slide bar caps 17 for the slide bar 16, the handle pin 23 has optional handle pin caps 34 for removable attachment to each end of the handle pin 23. The reverse is true for dissembling the instrument for sterilization or maintenance.

The handle may instead be a molded unit, with a limited number of removable parts. In that case, only the barrel section is dissembled for sterilization, and then reassembled. Since the handle is held by the physician outside the patient's body, it must be clean; however, since it is not in direct contact with the patient, it need not be sterile. The barrel section, though, enters the cervix and therefore must be sterile.

To assemble the instrument after sterilization, the user places the piston rod 14 into the hollow of the barrel 13. The end of the piston rod is somewhat shorter than (preferably approximately ⅔ of the length of) the barrel, so the piston rod does not extend to the end of the barrel. The user places the proximal ends of the piston rod 14 and barrel 13 into the second, central bore of the first handle portion 29. The user then slides the slide bar 16 through the fourth, oblong-shaped bore 32 of the second handle portion, through the first oblong-shaped bore 28 of the first handle portion, and then through the barrel bore 19 and the piston rod bore 15, and out the other side. Lastly, the user screws the slide bar caps 17 onto the ends of the slide bar 16.

Referring to FIG. 1, in addition to (a) the hollow barrel 13 with the open, distal end and a proximal end, and (b) the piston rod 14, which movably extends substantially through the barrel 13, the distal barrel section 12 comprises: (c) a cutting mechanism 35 coupled to the distal end of the barrel 13, which contains a movable surgical blade 36 for excising a tissue sample; and (d) a trigger mechanism 37, which is coupled to the cutting mechanism, for activating the movable blade. When the trigger mechanism 37 is pulled by the user, the movable blade 36 closes and excises the portion of soft tissue that is drawn into the distal barrel opening. The trigger mechanism 37 preferably comprises a trigger 38 attached to a trigger rod 39, and the trigger rod is preferably movably attached to the outside bottom of the barrel 13.

Referring to FIG. 2, the cutting mechanism 35 preferably further comprises a stationary blade 40 at the bottom (inferior portion) of the barrel 13. The movable blade is larger than the stationary blade. A straight, symmetrical, planar movable blade 36 having two opposite ends is preferred.

Figure 5:
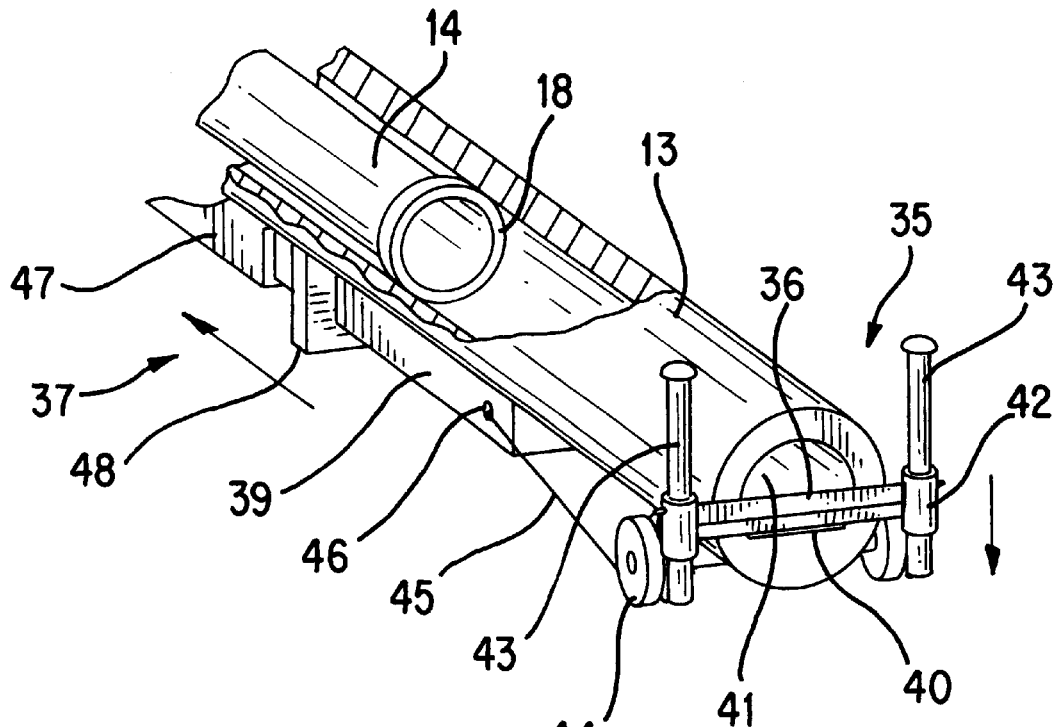
FIG. 5 is a front perspective view of the distal end of a biopsy instrument according to FIG. 4.

As shown in FIGS. 2 and 5, the cutting mechanism 35 is preferably a guillotine-type mechanism comprising:

(i) a generally planar (flat) movable blade 36, the movable blade having an open position above the barrel opening, as shown in FIG. 2, and a closed position at the bottom of the barrel opening 41, as shown in FIG. 5;

(ii) two matching slider posts 43, one on each side of the barrel opening, which are in parallel relationship to each other;

(iii) two matching slidable sleeves 42 at opposite ends of the movable blade 36, each slidable sleeve fitting closely around one slider post 43;

(iv) two matching, rotatable pulley wheels 44 below the barrel opening 41, one at the bottom of each slider post 43;

(v) one or two guide wires 45 movably attached at one end to each of the slidable sleeves 42 on either side of the movable blade 36. The guide wire is threaded around the pulley wheels, and affixed at an opposite end to or through the distal end of the trigger rod 39.

As shown in FIGS. 2 and 5, a single guide wire 45 is connected at one end to a slidable sleeve 42. From the slidable sleeve, it runs down through a groove along the center of the pulley wheel 44, then back through a trigger rod bore 46, which extends through the distal end of the trigger rod as shown in FIG. 2. On the other side of the trigger rod, the guide wire 45 continues through the groove on the other pulley wheel 44 and up to an attachment point on the other slidable sleeve 42. Where two guide wires 45 are utilized instead of one, one end of each guide wire 45 is attached to the slidable sleeve 42. The guide wire then threads through the pulley wheel 44 and extends back to the trigger rod. Its opposite end is attached to the distal end of the trigger rod 39. If two guide wires are used, there would be no trigger rod bore. The same is true of the guide wire 45 on the opposite side of the instrument 10.

Continuing with FIGS. 2 and 5, when the trigger 38 is pulled by the user, the trigger rod 39 retracts. This pulls the guide wires 45 back, which in turn pulls the slidable sleeves 42 down along the slider posts 43. This moves the movable blade 36 down to meet the stationary blade 40. The movable blade 36 is preferably approximately equal to or greater in length than the width of the barrel opening 41. The stationary blade 40 preferably is fitted into the bottom meniscus of the barrel opening. The trigger rod 39 preferably extends through a housing 47 at the base of the barrel. The trigger rod preferably has a trigger rod plate 48 at its distal end, which prevents the trigger rod from withdrawing too far and controls the amount that the movable blade will drop.

Figure 6:
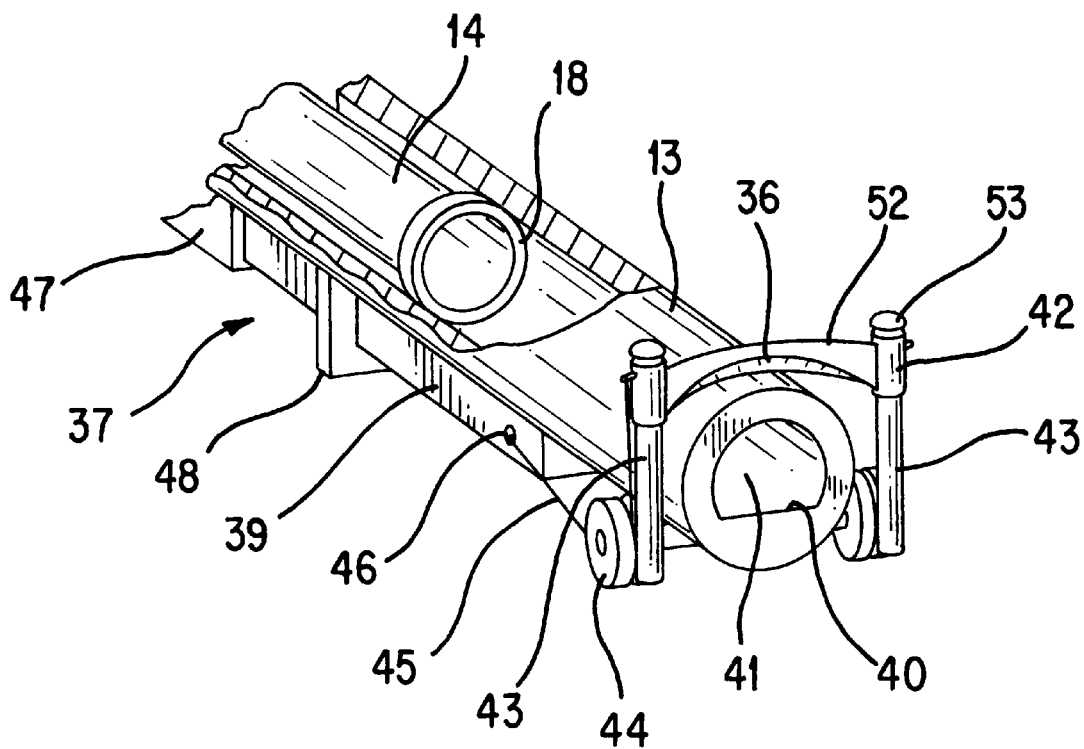
FIG. 6 is a front perspective view of the distal end of a first alternate embodiment of a biopsy instrument according to the present invention, having a curved upper blade.

With reference to FIG. 6, an alternate embodiment of the present invention is shown with a flat, arched movable blade 36 on the distal end of the barrel, rather than a rectangular-shaped movable blade. The movable blade 36, whether rectangular or crescent-shaped (arched), is preferably encased along its upper side by a thin, protective blade sheath 52. The lower, sharp blade edge on the opposite side of the movable blade is for excising the tissue samples. The stationary blade 40 or edge at the bottom of the distal end of the barrel 13 may also be arched, or straight as shown in FIG. 6. At the top of both slider posts 43 are preferred end caps 53 for preventing the slidable sleeves 42 from sliding off the end of the slider posts.

Figure 7:
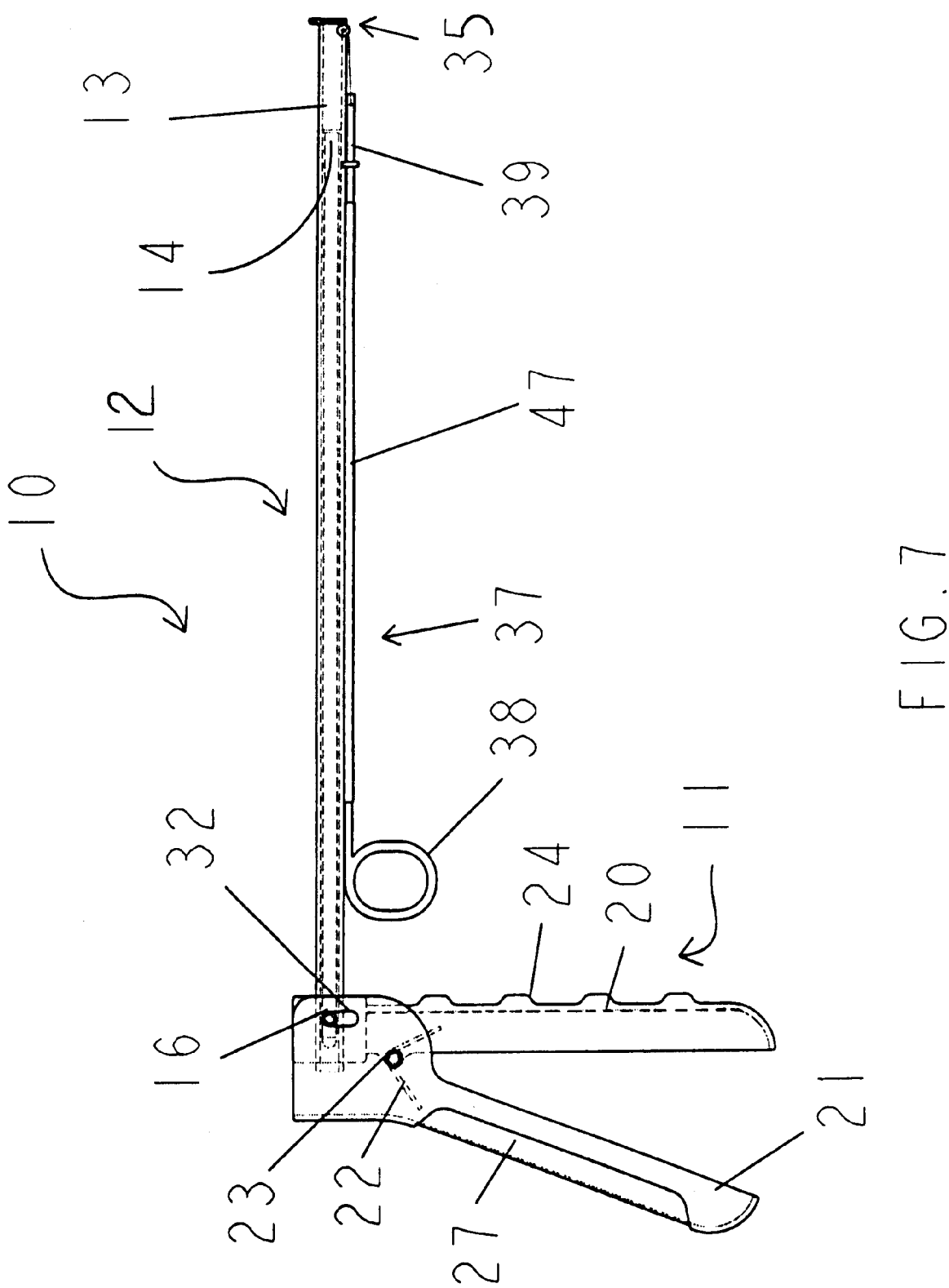
FIG. 7 is a side elevational view of a biopsy instrument according to the present invention, shown in an open position.
Figure 8:
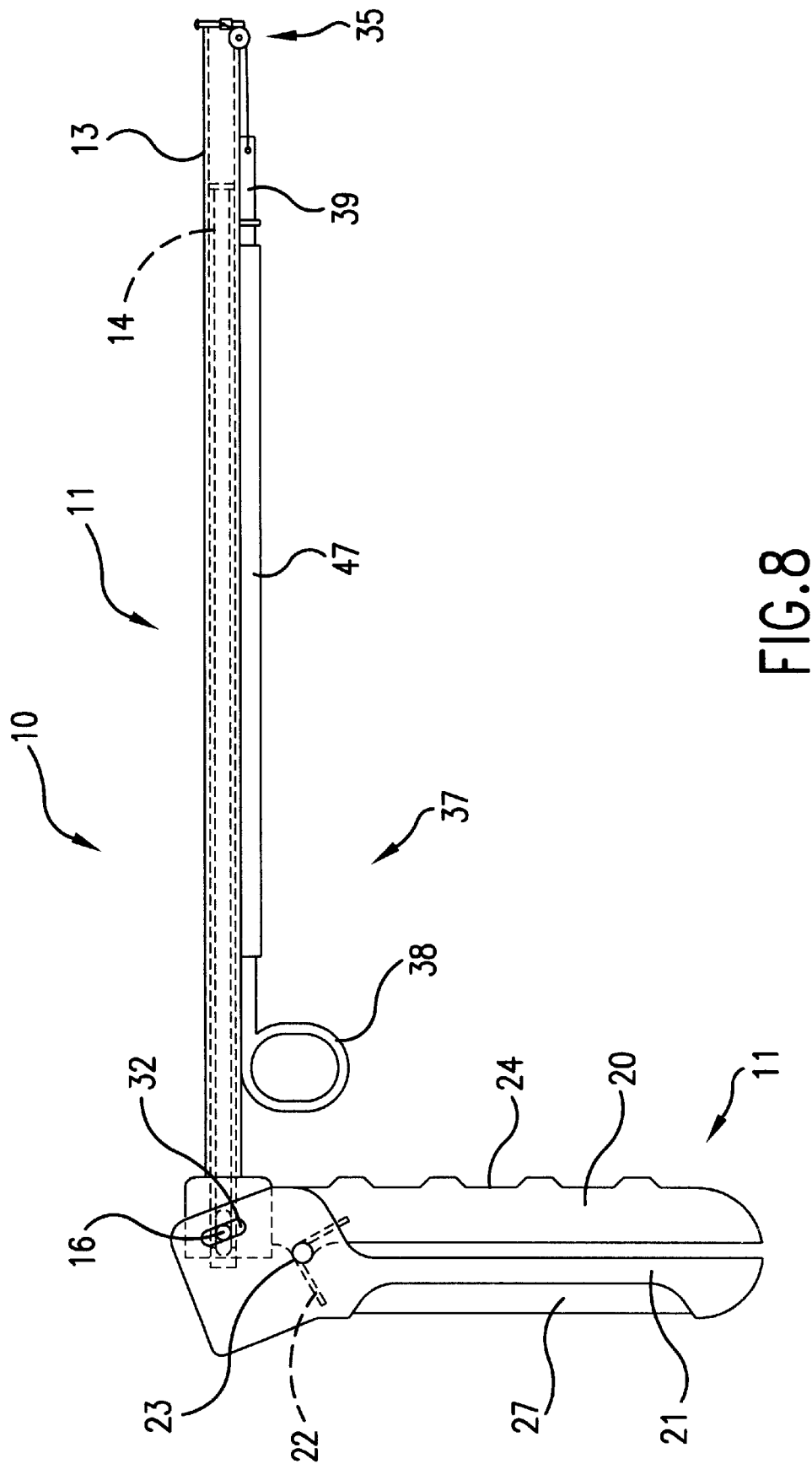
FIG. 8 is a side elevational view of a biopsy instrument according to FIG. 7, shown in a closed position.

Referring to FIGS. 7 and 8, the preferred embodiment of the instrument of the present invention is shown in side view. The handle section 11 is in an open, ready position in FIG. 7, and in a closed position, in FIG. 8. The internal action is also shown in dotted lines in FIGS. 7 and 8 for clarity. It can be seen that the piston rod 14 is retracted, or moved back, when the handle section is in the closed position. Grasping the handles and manually bringing them together will cause the second handle portion to rotate about an axis created by the handle pin. As the bottom of the second handle portion is rotated toward the first handle portion, the top part of the second handle portion rotates away from the barrel bringing the piston slide bar with it. This action produces the horizontal retractive force that withdraws the piston within the barrel creating suction at the barrels distal end.

The user would disassemble instrument and autoclave certain parts, including the barrel and the trigger rod. The distal barrel section 12 is removable from the proximal handle section 11, for separate autoclaving, or other sterilization, of the distal barrel section.

Referring to FIGS. 9 and 10, two alternate embodiments of the instrument are shown. The handle portions vary in ergonomic design, according to the desired grip. FIG. 11 shows a rear view of the embodiment shown in FIG. 10.

In regard to preferred dimensions, the distal barrel section 12 is between about five and seven inches in length, and between about ¼ and ¾ inch in width. The trigger rod 39 is preferably between about four and six inches in length, and about ⅛ to ½ inch in width and thickness. The handle section 11 is preferably between about five and seven inches in length, and about one and three inches in width. The cutting mechanism 35 is preferably between about ¼ and one inch in length and width, and approximately square. Tissue samples taken with this instrument 10 will be approximately round in shape, and between about ⅛ and ¼ inch in diameter.

In FIGS. 9 and 10, a threaded rod 49 extends from the proximal surface of the first handle portion 20 back through a corresponding threaded aperture in the second handle portion 21. The threaded rod 49 is threaded through a threaded hole in the center of a small, rotatable disk 50. The user rotates the disk 50 to indirectly adjust the amount of movement of the piston rod 14, and therefore control the amount of suction in the distal end of the barrel hollow. As the threaded, rotatable disk 50 is advanced towards the second handle portion 21, the degree to which the handle can close against the first handle position is increased. Ultimately, this lessens the amount of piston withdrawal, thus decreasing the force of suction at the distal end of the barrel 13.

In sum, the proximal handle section further comprises: (1) the threaded rod 49 extending from the first handle portion 20 through the central, threaded aperture in the second handle portion 21; and (2) the rotatable disk 50 threaded onto the threaded rod between the first and second handle portions 20, 21; wherein the rotatable disk can be rotated clockwise or counterclockwise to regulate movement of the piston rod 14, and therefore the amount of suction in the distal end of the barrel.

Figure 12:
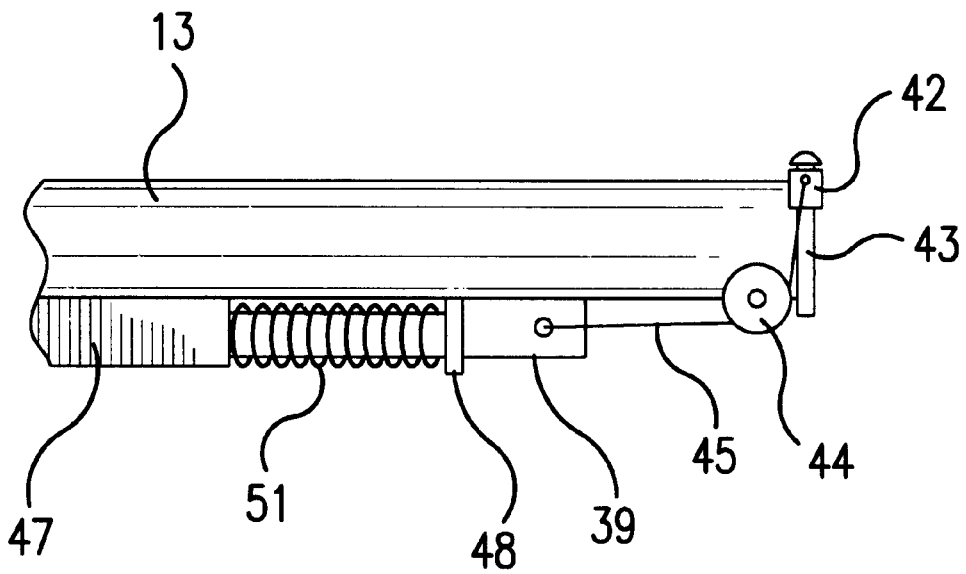
FIGS. 12 and 13 are side elevational close-up views of the distal end of a fourth alternate embodiment of a biopsy instrument according to the present invention, shown in open and closed positions, respectively.
Figure 13:
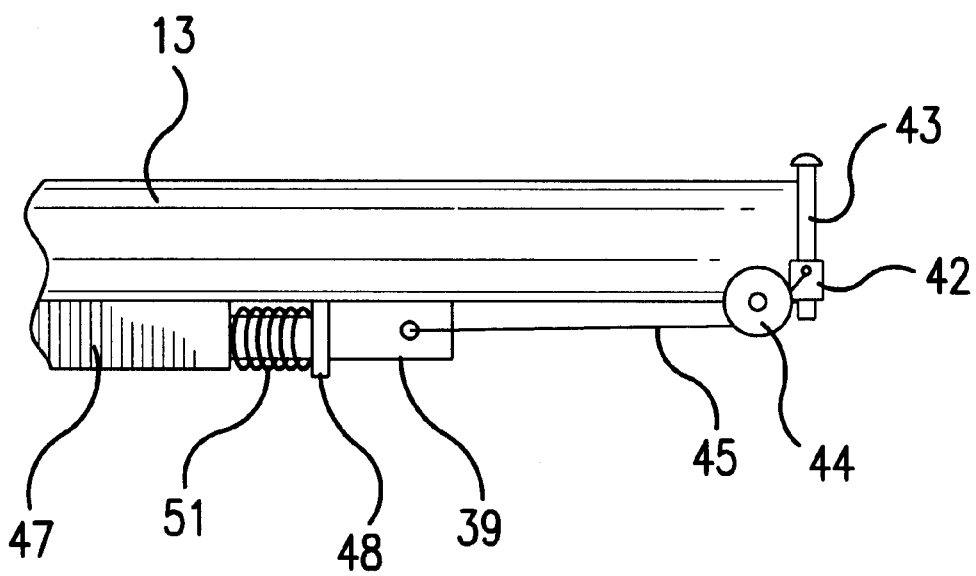

Referring to FIGS. 12 and 13, close-up views of the distal end of the trigger rod 39 shows a trigger rod coil spring 51 around the distal end of the trigger rod 39 between the trigger rod guide 48 and the distal end of the trigger rod housing 47. This tension coil spring 51 allows the movable blade 36 to return to the up or open position between biopsies, and facilitates the removal of the tissue specimen from the barrel opening 41 once the distal end of the instrument 10 is withdrawn from the patient. In FIG. 12, the movable blade is in the open position, and in FIG. 13, the movable blade is in the closed position.

In sum, a preferred embodiment of the instrument 10 further comprises:
(i) a housing 47 underneath, and parallel to, the barrel 13 through which the trigger rod 39 slidably extends;
(j) a trigger rod guide 48 extending around the distal end of the trigger rod 39 for preventing withdrawal of the distal end of the trigger rod through the housing 47; and
(k) a tension coil spring 51 coiled loosely around the trigger rod 39 between the trigger rod plate 48 and the distal end of the trigger rod housing 47. The coil spring 51 has a proximal end and a distal end. The housing 47 is substantially shorter in length than the trigger rod 39. The trigger rod is preferably not removed from the housing for autoclaving/cleaning. The distal end of the coil spring 51 rests against the trigger rod guide 48 and the proximal end of the coil spring rests against the distal end of the housing. The coil spring requires the user to pull the trigger 38 to create a sufficient force to overcome the tension spring in order to withdraw the trigger mechanism, which allows the movable blade 36 to draw down. Once the trigger is released, the coiled spring 51 causes the trigger and connecting blade apparatus to revert to its previous open position.

From the foregoing it can be realized that the described instrument of the present invention may be easily and conveniently utilized for performing soft tissue biopsies. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A surgical instrument for biopsying soft body tissue, which comprises:
   (1) a distal barrel section, which comprises:
      a hollow barrel having an open, distal end and an opposite proximal end;
      a piston rod which movably extends substantially through the barrel, the piston rod having a distal end and an opposite proximal end;
      a cutting mechanism coupled to the distal end of the barrel, the cutting mechanism comprising a movable surgical blade for excising a tissue sample, and having an open, ready position and a closed position;
      a trigger mechanism coupled to the cutting mechanism for moving the movable blade; and
   (2) a proximal handle section coupled to the proximal ends of both the barrel and the piston rod; and
   wherein the proximal handle section is compressed to retract the piston rod from the distal end of the barrel creating suction within the distal end of the barrel;
   wherein the trigger mechanism is pulled to move the cutting mechanism from the open position to the closed position.

2. An instrument according to claim 1, wherein the distal barrel section is removable from the proximal handle section, for separate sterilization of the distal barrel section.

3. An instrument according to claim 1, wherein the proximal handle section comprises:
   a first handle portion having an upper and a lower end, the upper end being coupled to the proximal ends of the barrel and the piston rod;
   a second handle portion coupled at an upper end to the upper end of the first handle section;
   a spring mechanism pivotally engaged between the first and second handle sections; and
   wherein the piston rod is moved in a proximal direction when the first and second handle portions are squeezed toward each other.

4. An instrument according to claim 3, wherein the proximal handle section is compressed to move the piston rod away from the distal end of the barrel and create suction within the distal end of the barrel, thereby drawing soft body tissue into the open distal end of the barrel; and wherein the movable blade is adapted to close and excise a portion of soft body tissue occluding the open distal end of the barrel when the trigger mechanism is pulled.

5. An instrument according to claim 3, wherein the distal barrel section further comprises:
   a slide bar at the proximal end of the piston rod which movably extends through a bore in the piston rod, in a direction perpendicular to the piston rod.

6. An instrument according to claim 5, wherein the first and second handle portions each comprise a matched set of shoulders, with a similarly sized pin bore through each shoulder; wherein the spring mechanism is movably affixed between the corresponding shoulders of the first and second handle portions; and wherein the proximal handle portion further comprises:
   a movable pin inserted through the matched sets of pin bores in the corresponding shoulders of the first and second handle portions and through the spring mechanism.

7. An instrument according to claim 6, wherein the upper end of the first handle portion further comprises a second, central bore through which extends the proximal ends of the barrel and the piston rod; wherein the first handle portion comprises a third, oblong-shaped bore which is perpendicular to, and intersects with, the second, central bore; wherein the second handle portion comprises a matching set of fourth, oblong-shaped bores; and wherein the slide bar movably extends through the third and fourth, oblong-shaped bores in the first and second handle portions, and through the bores in the proximal ends of the barrel and piston rod.

8. An instrument according to claim 7, wherein an oblong shape of a first bore of the first handle portion extends in a horizontal direction, while the oblong shapes of the matching, fourth bores in the second handle portion extend in a vertical direction, and wherein the piston rod moves in a backward, proximal direction when the handle portions are squeezed towards each other, and returns to a forward, resting position when the handle portions are released.

9. An instrument according to claim 1, wherein the cutting mechanism further comprises a stationary blade at a lower portion of the open distal end of the barrel section.

10. An instrument according to claim 9, wherein the trigger mechanism comprises a trigger attached to a trigger rod, the trigger rod being movably attached to the outside bottom of the barrel.

11. An instrument according to claim 10, wherein the cutting mechanism comprises:
   a generally planar movable blade having an open, ready position above the open distal end of the barrel, and a closed position at the bottom of the open distal end of the barrel;
   two matching slider posts, one on each side of the open distal end of the barrel, which are in parallel relationship to each other;
   two matching, slidable sleeves at opposite ends of the movable blade, each slidable sleeve fitting closely around one slider post;
   two matching, rotatable pulley wheels below the open distal end of the barrel, one at the bottom of each slider post;
   one or two guide wires movably attached at each end to each slidable sleeve, the guide wire being threaded around the pulley wheels, and affixed at an opposite end to or through the distal end of the trigger rod; and wherein, when the trigger is pulled the trigger rod retracts, which pulls the guide wires back, which in turn pulls the slidable sleeves down along the slider posts, which moves the movable blade down to meet the stationary blade.

12. An instrument according to claim 11, wherein the movable blade is rectangular-shaped and protected along its upper edge by a blade sheath.

13. An instrument according to claim 12, further comprising removable caps for covering the opposite ends of the slide bar and the handle pin.

14. An instrument according to claim 11, wherein the movable blade is arched, and the movable blade is larger than the stationary blade.

15. An instrument according to claim 11, wherein the proximal handle section further comprises:

a threaded rod extending from the first handle portion through a central, threaded bore in the second handle portion; and a rotatable disk threaded onto the threaded rod between the first and second handle portions;

wherein the rotatable disk is adapted to control movement of the piston rod, and therefore the amount of suction in the distal end of the barrel.

16. An instrument according to claim 11, and further comprising:

a housing underneath, and parallel to, the barrel through which the trigger rod slidably extends, the trigger rod housing being substantially shorter in length than the trigger rod;

a trigger rod guide extending around the distal end of the trigger rod for preventing withdrawal of the distal end of the trigger rod through the housing; and a coil spring coiled loosely around the trigger rod, the coil spring having a proximal end and a distal end, the distal end of the coil spring resting against the trigger rod guide and the proximal end of the coil spring resting against the distal end of the housing, for causing the trigger and movable blade to return to the open position when the trigger is released.

* * * * *